(12) United States Patent
Pastecki et al.

(10) Patent No.: US 9,146,181 B2
(45) Date of Patent: Sep. 29, 2015

(54) SYSTEM AND METHOD FOR CONTAMINANT DETECTION IN FLUID STREAMS

(75) Inventors: Patrick Edward Pastecki, Pearland, TX (US); Joe Schornick, Pearland, TX (US); Michal Marek Knapczyk, Warsaw (PL)

(73) Assignee: Generel Electric Company, Schenectady, NY (US)

( * ) Notice: Subject to any disclaimer, the term of this patent is extended or adjusted under 35 U.S.C. 154(b) by 305 days.

(21) Appl. No.: 13/696,298

(22) PCT Filed: Jul. 27, 2012

(86) PCT No.: PCT/PL2012/000059
§ 371 (c)(1),
(2), (4) Date: Nov. 5, 2012

(87) PCT Pub. No.: WO2014/017932
PCT Pub. Date: Jan. 30, 2014

(65) Prior Publication Data
US 2014/0026636 A1    Jan. 30, 2014

(51) Int. Cl.
G01N 7/00 (2006.01)
G01N 1/22 (2006.01)
G01N 17/00 (2006.01)
G01N 33/22 (2006.01)
G01N 33/28 (2006.01)

(52) U.S. Cl.
CPC ............... *G01N 1/22* (2013.01); *G01N 17/008* (2013.01); *G01N 33/222* (2013.01); *G01N 33/225* (2013.01); *G01N 33/28* (2013.01)

(58) Field of Classification Search
USPC .............. 73/23.2, 23.33, 28.01, 31.02, 31.03, 73/61.71
See application file for complete search history.

(56) References Cited

U.S. PATENT DOCUMENTS

| 8,323,980 B2 | 12/2012 | Boday et al. |
| 2002/0108911 A1 | 8/2002 | Xiong |
| 2004/0031268 A1 | 2/2004 | Wilkes |

(Continued)

FOREIGN PATENT DOCUMENTS

GB    2292607 A    2/1996

OTHER PUBLICATIONS

Otsuka, Nubuo. "A thermodynamic approach on vapor-condensation of corrosive salts from flue gas on boiler tubes in waste incinerators", Corrosion Science vol. 50, No. 6, pp. 1627-1636, XP022698969, ISSN: 0010-938X, Jun. 1, 2008.

(Continued)

*Primary Examiner* — Peter Macchiarolo
*Assistant Examiner* — Mohammed Keramet-Amircola
(74) *Attorney, Agent, or Firm* — Fletcher Yoder, P.C.

(57) ABSTRACT

A contaminant detection system has a fluid path. A meter and a plurality of fluid conduits are disposed along the fluid path. The meter is configured to detect an operating parameter of a fluid. The plurality of fluid conduits forms a plurality of intermediate fluid paths. Each fluid conduit has a restriction orifice (RO), an inlet control valve, and an outlet control valve. In addition, the plurality of fluid conduits has a control line and an exposed line. The control line is configured to be isolated from the fluid for a time period. The exposed line is configured to be exposed to the fluid for the time period. The system is configured to determine a contaminant concentration of the fluid at least in part using the operating parameter and the time period.

20 Claims, 3 Drawing Sheets

(56) References Cited

U.S. PATENT DOCUMENTS

| | | |
|---|---|---|
| 2007/0072137 A1 | 3/2007 | Peluso |
| 2008/0283382 A1 | 11/2008 | Al-Taie et al. |
| 2009/0148800 A1* | 6/2009 | Valentas et al. ................. 431/13 |
| 2010/0021371 A1* | 1/2010 | Prim et al. ................. 423/578.1 |
| 2011/0146800 A1* | 6/2011 | Jallon et al. ....................... 137/1 |
| 2012/0103185 A1 | 5/2012 | Vaidya et al. |

OTHER PUBLICATIONS

Search Report and Written Opinion from corresponding International Application No. PCT/PL2012/000059, dated Jan. 14, 2013.

* cited by examiner

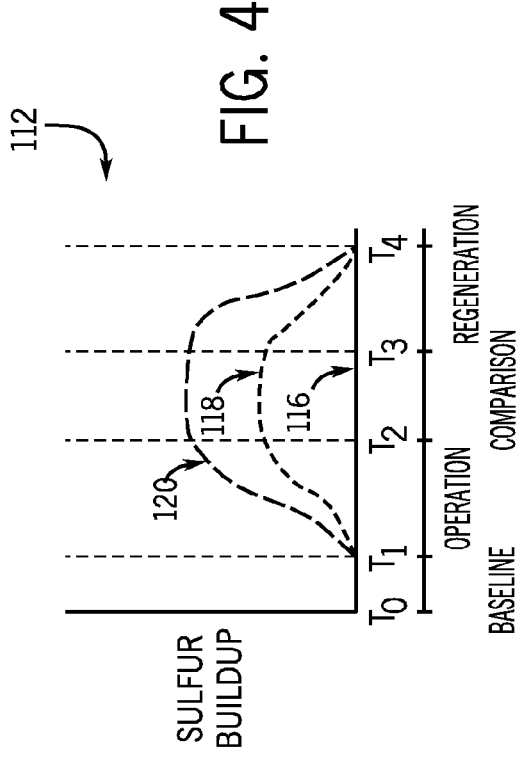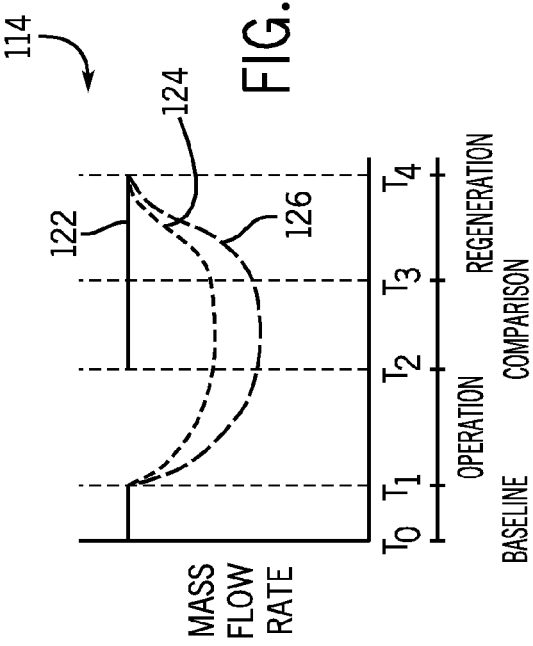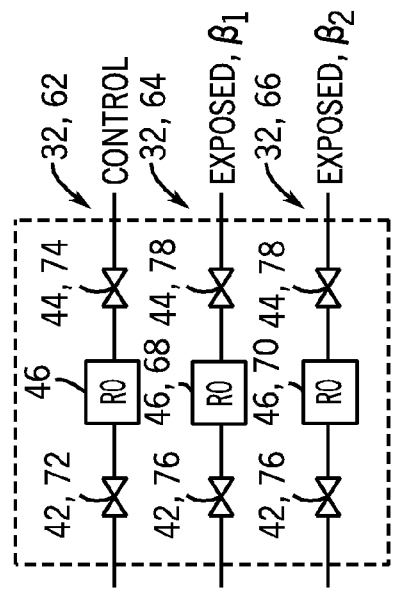

SYSTEM AND METHOD FOR CONTAMINANT DETECTION IN FLUID STREAMS

CROSS-REFERENCE TO RELATED APPLICATIONS

This application is a Non-Provisional Application of International Patent Application No. PCT/PL2012/000059, entitled "System and Method for Contaminant Detection in Fluid Streams", filed Jul. 27, 2012, which is herein incorporated by reference in its entirety.

BACKGROUND OF THE INVENTION

The subject matter disclosed herein relates generally to detecting impurities, and more specifically, to systems and methods for detecting contaminants within a fluid stream.

Contaminants (e.g., elemental sulfur and sulfur-containing compounds) may be present within fluid streams in a variety of applications, such as in a wellhead of an oil or gas production system, in a pipeline of an oil or gas supply and distribution system, or in a combustor of a gas turbine. Sulfur deposition may occur within these applications, even when the sulfur concentration is low (e.g., 10 parts per billion by volume). For example, the sulfur deposits may form restrictions at the throats of fuel control valves, bends in pipelines, and other restrictions in a fluid flow path. Unfortunately, these sulfur deposits may lead to decreased fluid production rates, increased corrosion rates, and/or higher filtration costs in these applications. Sulfur detection, particularly for trace amounts of sulfur, may be difficult and time-consuming.

BRIEF DESCRIPTION OF THE INVENTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a contaminant detection system includes a fluid path configured to flow a fluid comprising a contaminant concentration. A meter and a plurality of fluid conduits are disposed along the fluid path. The meter is configured to detect an operating parameter of a fluid. The plurality of fluid conduits forms a plurality of intermediate fluid paths configured to flow the fluid. Each fluid conduit of the plurality of fluid conduits includes a restriction orifice (RO), an inlet control valve, and an outlet control valve. The RO has an orifice diameter and is configured to constrict flow of the fluid. The inlet control valve is disposed upstream of the RO, and the outlet control valve is disposed downstream of the RO. In addition, the plurality of fluid conduits has a control line and a first exposed line. The control line is configured to be isolated from the fluid for a time period. The first exposed line is configured to be exposed to the fluid for the time period. In addition, the contaminant detection system is configured to estimate the contaminant concentration using at least the operating parameter and the time period.

In a second embodiment, a method includes selecting a control line and an exposed line from a plurality of fluid conduits using a controller, and detecting a baseline operating parameter for the control line and the exposed line using a meter. The method also includes isolating the control line for a time period using one or more control valves, and exposing the exposed line for the time period using the one or more control valves. In addition, the method includes detecting a first operating parameter through the control line using the meter, detecting a second operating parameter through the exposed line using the meter, and determining a contaminant concentration of a fluid based at least in part on the first operating parameter, the second operating parameter, the baseline operating parameter, and the time period.

In a third embodiment, a sulfur detection system includes a fluid path configured to flow a fluid comprising a sulfur concentration. A flow meter is disposed along the fluid path and is configured to detect a flow rate of a fluid. A control line defines a first intermediate fluid path. The control line has a first restriction orifice (RO) configured to constrict the first intermediate fluid path, a first inlet control valve disposed upstream of the first RO, and a first outlet control valve disposed downstream of the first RO. Similarly, the exposed line defines a second intermediate fluid path. The exposed line has a second restriction orifice (RO) configured to constrict the intermediate fluid path and is configured to capture sulfur from the fluid, a second inlet control valve disposed upstream of the second RO, and a second outlet control valve disposed downstream of the second RO. The sulfur detection system also includes a controller communicatively coupled to the first and second inlet control valves and the first and second outlet control valves. The controller is configured to selectively isolate or expose the control line and the exposed line by adjusting the first and second inlet control valves and the first and second outlet control valves. In addition, the control line is configured to be isolated from the fluid for a time period, the exposed line is configured to be exposed to the fluid for the time period, and the controller is configured to determine a sulfur concentration of the fluid based at least in part on the flow rate and the time period.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 3 is a schematic diagram of an embodiment of a portion of the sulfur detection system of FIG. 2;

FIG. 4 is a graphical illustration showing sulfur buildup over time for the sulfur detection system of FIG. 3;

FIG. 5 is a graphical illustrating showing mass flow rates over time for the sulfur detection system of FIG. 3.

DETAILED DESCRIPTION OF THE INVENTION

Figure 1:
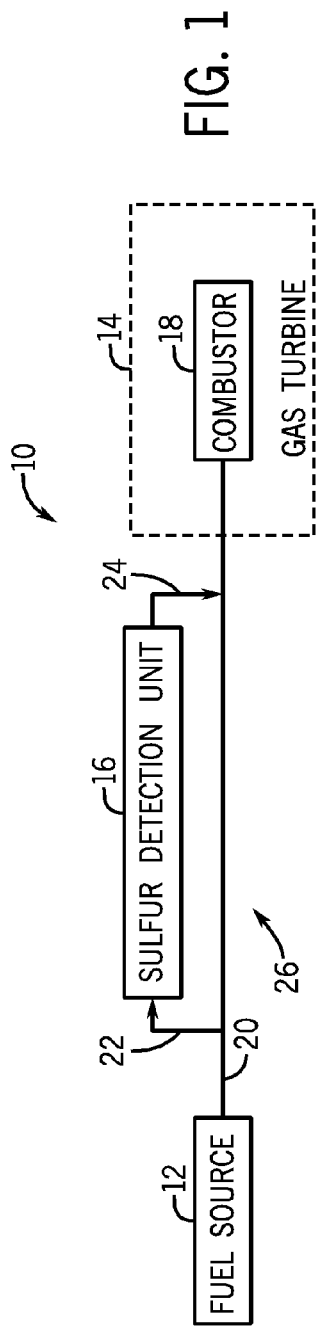
FIG. 1 is a schematic diagram of an embodiment of a system having a fuel source, an end user of the fuel, and a sulfur detection system disposed therebetween.

One or more specific embodiments of the invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the invention, the articles "a," "an," "the," and "said" are intended to mean that there are one or more of the elements. The terms "comprising," "including," and "having" are intended to be inclusive and mean that there may be additional elements other than the listed elements. In addition, the term "sulfur" is intended to include elemental sulfur as well as sulfur-containing compounds.

The present disclosure is directed toward systems and methods to quickly detect contaminants (e.g., sulfur, metal oxides, etc.) within fluid streams (e.g., gas streams or liquid streams). Although the ensuing discussion is directed towards sulfur detection, it should be noted that the present techniques may be applied to detect a variety of contaminants and are not limited to sulfur. In addition, the present techniques may be applied to a gas-phase stream, a liquid-phase stream, or a mixed-phase stream with gas and liquid. In a presently contemplated embodiment, a sulfur detection system may detect a sulfur concentration of a fluid stream by inducing sulfur deposition into an exposed line. The deposited sulfur from the fluid stream may alter the geometry of the exposed line, resulting in a decreased flow rate of the fluid through the exposed line. In addition, a control line that is isolated from the fluid stream may create a baseline for comparison with the exposed line. For example, a sulfur concentration of the gas stream may be determined by comparing the respective flow rates of the fluid through the control line and the exposed line. Further, it is now recognized that the use of a smaller geometry for the exposed line compared to the geometry of large scale valves or infrastructure advantageously results in a more rapid detection of sulfur deposition for equivalent periods of exposure and subsequent detection. That is, geometry changes within the exposed line are more readily detectable as compared to geometry changes within larger infrastructure. Indeed, faster detection may enable faster responses to the undesirable operating conditions. That is, operating parameters of upstream or downstream equipment may be adjusted in response to the detected sulfur concentration, thereby improving production rates and decreasing corrosion rates. For example, if the detected sulfur concentration is within a predetermined range (e.g., exceeds a threshold value), the temperature of upstream or downstream equipment may be increased to mitigate sulfur deposition.

Turning now to the figures, FIG. 1 illustrates a system 10 having a fuel source 12, a fuel application (e.g., a gas turbine 14), and a sulfur detection system 16 disposed therebetween. In certain embodiments, the fuel source 12 may supply a gaseous or liquid fuel, such as synthetic gas produced by a gasifier, natural gas, raw oil, and the like. For example, the fuel source 12 may be a gas production well, a storage vessel, a truck, a fluid treatment system (e.g., an acid gas removal system of a synthetic gas production facility), or any combination thereof. In addition, the end user may be a combustor 18 of the gas turbine 14, an internal combustion engine, a boiler, a furnace, a power plant, a chemical plant, or another suitable end user of a hydrocarbon fluid. As illustrated, a gas transportation system (e.g., a pipeline 20) couples the fuel source 12, the gas turbine 14, and the sulfur detection system 16. In certain embodiments, the sulfur detection system 16 may be mounted to the pipeline 20. As illustrated, the sulfur detection system 16 is arranged in parallel with the pipeline 20.

The sulfur detection system 16 may route slip streams of fluid from the pipeline 20 through a sample line 22 to determine a sulfur concentration of the fluid. The sulfur detection system may subsequently return the slip stream of the fluid to the pipeline 20 through a line 24. For example, fluid may flow through a fluid path 26 that includes the fuel source 12, the sulfur detection system 16, and the gas turbine 14. As will be discussed further below with respect to FIG. 2, the sulfur detection system 16 includes components for detecting a sulfur concentration of the fluid samples flowing through the sample line 22. Operation of the fuel source 12 or the gas turbine 14 may be adjusted based on the detected sulfur concentration. Accordingly, early detection of sulfur may increase the operability of the fuel source 12 and the gas turbine 14, and may also reduce the possibility of corrosion within the pipeline 20.

Figure 2:
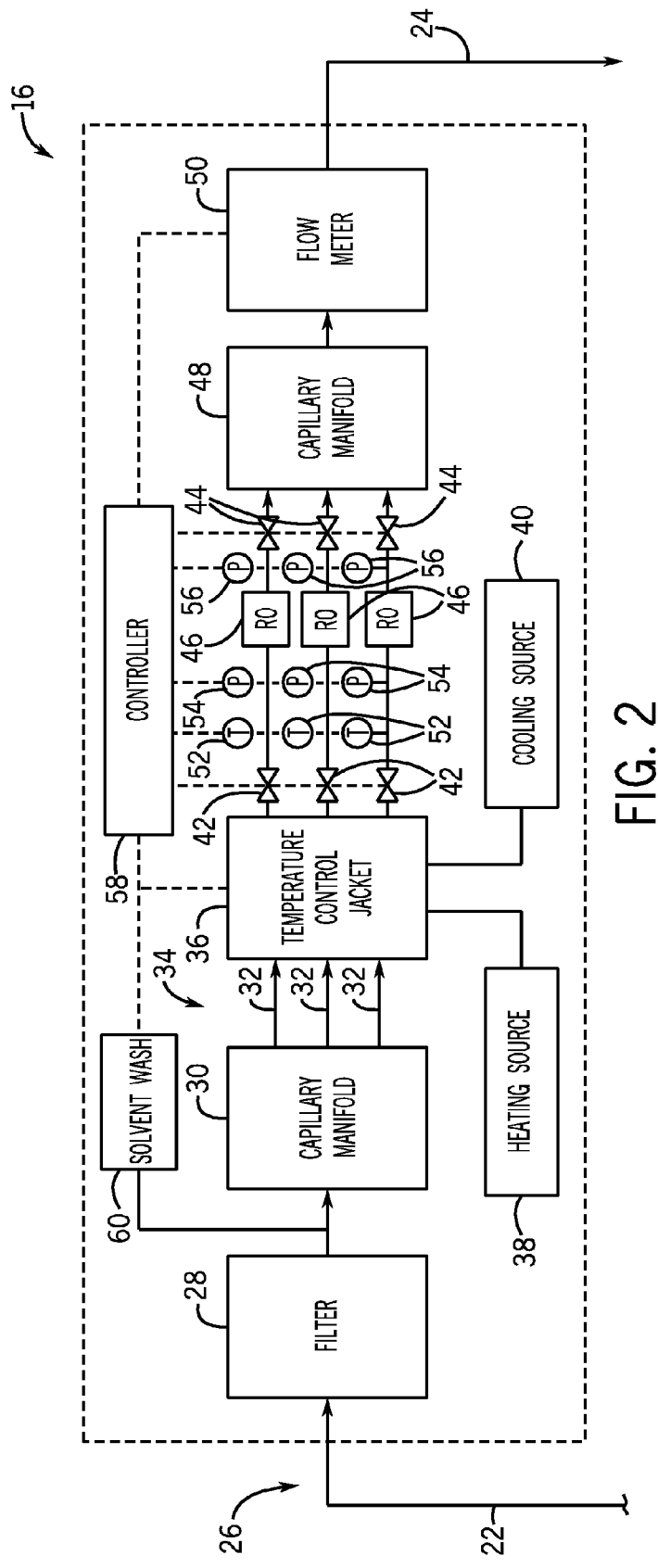
FIG. 2 is a schematic diagram of an embodiment of the sulfur detection system of FIG. 1.

FIG. 2 is a schematic diagram illustrating multiple components of an embodiment of the sulfur detection system 16. As noted above, the sulfur detection system 16 may encourage sulfur deposition into an exposed line in order to quickly detect sulfur concentrations of a fluid stream. The deposited sulfur from the fluid may alter the geometry of (e.g., constrict) the exposed line, resulting in a decreased flow rate through the exposed line. In addition, the altered geometry may accelerate sulfur deposition, further decreasing the flow rate. In accordance with present embodiments, a sulfur concentration of the fluid may be estimated based on the flow rate through the exposed line over time.

As shown, a filter 28 may be disposed along the fluid path 26. During operation of the system 10, the filter 28 may remove an impurity, such as a particulate, from the fluid, thereby increasing the operability of the sulfur detection system 16. For example, the filter 28 may be a pneumatic filter, a membrane, or a combination thereof. After filtration, the fluid may flow through an inlet capillary manifold 30 disposed downstream of the filter 28. The inlet capillary manifold 30 directs the fluid into a plurality of fluid conduits 32. In other words, each fluid conduit 32 forms an intermediate fluid path 34 that the fluid may selectively flow through. That is, the fluid may selectively flow through a single fluid conduit, or any combination of the fluid conduits 32. The illustrated sulfur detection system 16 includes 3 fluid conduits 32, forming a total of 3 intermediate fluid paths 34. However, the number of fluid conduits 32 may vary. For example, the sulfur detection system 16 may include 2, 3, 4, 5, 6, or more fluid conduits 32.

Each fluid conduit 32 has an inner diameter that defines a flowing area for the fluid. The inner diameter of certain fluid conduits 32 may vary, enabling varying amounts of fluid to flow through the intermediate fluid paths 34, thereby increasing the operability of the sulfur detection system 16. For example, a fluid conduit 32 may have an inner diameter of 0.5 mm, whereas another fluid conduit 32 has an inner diameter of 3 mm. Additionally or alternatively, the inner diameters of the fluid conduits 32 may be based on an inner diameter of the pipeline 20. For example, a ratio of the inner diameter of the fluid conduit 32 to the inner diameter of the pipeline 20 may be between approximately 0.00003 to 0.3, or 0.001 to 0.1. As noted earlier, the smaller geometry of the fluid conduit 32 as compared to the pipeline 20 may enable rapid sulfur deposition within the fluid conduit 32 and rapid sulfur detection by the sulfur detection system 16.

In the illustrated embodiment, the sulfur detection 16 system also includes a temperature control jacket 36. Although the temperature control jacket 36 is depicted as downstream of the inlet capillary manifold 30, the temperature control jacket 36 may be disposed upstream of the inlet capillary manifold 30 or the filter 28. The temperature control jacket 36 surrounds each of the fluid conduits 32 and selectively adjusts the temperature of the fluid within the fluid conduits 32. That is, the temperature control jacket 36 may independently increase, decrease, or maintain the temperature of the fluid within each of the fluid conduits 32, based on the operating parameters of the sulfur detection system 16. As illustrated, the temperature control jacket 36 is coupled to a heating source 38 and a cooling source 40. The heating source 38 provides heat to the temperature control jacket 36 and to the fluid within the fluid conduits 32. In certain embodiments, the heating source 38 may be steam (e.g., steam tracing), electricity (e.g., resistive heating), a heat exchange fluid (e.g., exhaust gas, heated water, etc.), or any other suitable heat source. Similarly, the cooling source 40 provides cooling to the temperature control jacket 36 and to the fluid within the fluid conduits 32. In certain embodiments, the cooling source may be a cooling fluid (e.g., cooling water, solvent, inert gas, air, etc.), a convective cooler, or any other suitable cooling source. However, certain embodiments may not include the temperature control jacket 36. In such an embodiment, the fluid may be cooled by expansion cooling. For example, the pressure of the fluid may be decreased by throttling one or more valves, which induces a temperature drop of the fluid. As will be discussed further below, the temperature control jacket 36 provides selective heating and cooling to improve the operability of the sulfur detection system 16. For example, cooling the fluid conduits 32 may accelerate sulfur deposition (e.g., deposition out of the fluid), enabling a more rapid detection of sulfur. In addition, heating the fluid conduits 32 after sulfur deposition may regenerate the fluid conduits 32 for further use by re-dissolving the sulfur into the fluid (e.g., enhancing the solubility of the sulfur in the fluid). Thus, regeneration of the fluid conduits 32, as discussed herein, is intended to denote treating the fluid conduits 32 using heat, the fluid, solvent, etc., to a geometry (e.g., diameter) and/or chemistry (e.g., surface state) that is substantially the same as the fluid conduits 32 prior to exposure to the fluid having the sulfur.

Each fluid conduit 32 includes an inlet control valve 42, an outlet control valve 44, and a restriction orifice (RO) 46 disposed therebetween. The control valves 42 and 44 enable each fluid conduit 32 to be independently isolated. As discussed below, such independent isolation enables at least one of the fluid conduits 32 to be used as a control line, while the remaining fluid conduits 32 are used as test lines (i.e., exposed lines). The control line may define a baseline flow, and the baseline flow may be used to determine a sulfur concentration of the fluid. The control valves 42 and 44 may be used to isolate the control line, creating a basis of comparison for the flow rates of the fluid within the exposed lines.

The RO 46 of each fluid conduit 32 may be any feature that creates a constriction in the fluid conduit 32, such as a venturi or a thin metal, glass, ceramic, or composite plate with a hole. When fluid reaches the RO 46, the fluid is forced to flow through the hole. Accordingly, the RO 46 may constrict the intermediate fluid paths 34 to encourage sulfur deposition, depending on the geometry of the hole. For example, fluid flowing through the RO 46 may cause a localized pressure drop with associated expansion cooling, resulting in sulfur deposition on the RO 46. As sulfur deposits on the RO 46, the geometry of the RO 46 may change, further constricting the intermediate fluid path 34 and decreasing the flow rate of the fluid. A calibration curve may enable estimation of the sulfur concentration of the fluid as a function of the flow rate and/or the sulfur deposition rate, among other variables. Advantageously, measuring sulfur deposition on the RO 46 has a high resolution and high accuracy.

The geometry (e.g., size, shape, bevel, and the like) of the RO 46 may vary according to implementation-specific embodiments. For example, the hole of the RO 46 may be circular, square, beveled, or another suitable shape. In addition, the hole of the RO 46 may be centered on the metal plate (e.g., concentric), or the hole may be offset from the center (e.g., eccentric). In certain embodiments, the diameter of the hole (i.e., orifice diameter) may be based on the inner diameter of the fluid conduit 32. For example, a ratio (i.e. $\beta$ ratio) of the orifice diameter to the inner diameter of the fluid conduit 32 may be between approximately 0.01 to 0.99, 0.1 to 0.9, or 0.3 to 0.7. In certain embodiments, the corresponding orifice diameter may be approximately 0.01 inches, 0.016 inches, or 0.024 inches. The orifice diameter may be designed to achieve a desired rate of sulfur deposition on the RO 46.

In certain embodiments, it may be desirable to vary the orifice diameter of certain ROs 46 within the sulfur detection system 16, to vary the sulfur deposition rates within each fluid conduit 32. For example, an RO 46 may have a $\beta$ ratio of approximately 0.3, and another RO 46 may have a $\beta$ ratio of approximately 0.7. In such a case, sulfur deposition may occur at different rates in each RO 46, resulting in varying flow rates through the fluid conduits 32. The varying flow rates may be used to calculate an approximate sulfur concentration of the fluid. For example, a calibration curve may be based on a flow rate, a geometry of the RO 46 (e.g., orifice diameter), and the time period over which sulfur deposition occurs. Estimation of sulfur concentration may be based on the calibration curve and the observed flow rate through any one or a combination of the fluid conduits 32.

After flowing through the RO 46 and the outlet control valve 44, the fluid may continue along the fluid path 26 to an outlet capillary manifold 48. The outlet capillary manifold 48 receives fluid from each of the fluid conduits 32, merges the respective flows together into a single stream, and returns the single stream to the pipeline 20 via the line 24. In the illustrated embodiment, a meter (e.g., flow meter 50) is disposed downstream of the outlet capillary manifold 48. The flow meter 50 may detect a flow rate (e.g., mass flow or volumetric flow) of the fluid exiting the sulfur detection system 16. In certain embodiments, the flow meter 50 may be a coriolis flow meter, a thermal mass flow meter, or any other suitable meter. In addition, the number of flow meters 50 and their respective locations may vary. For example, the sulfur detection system 16 may include 1, 2, 3, 4, 5, or more flow meters 50. Each of the fluid conduits 32 may have a dedicated flow meter 50, enabling the intermediate fluid flows to be independently monitored and controlled. Indeed, an arrangement with multiple flow meters 50 may further increase the operability of the sulfur detection system 16. For example, the sulfur detection system 16 may have a backup flow meter 50, or the multiple flow meters 50 may enable the exclusion of data that does not accord with flow measurements from other flow meters to increase the reliability of the flow measurements. Although the ensuing discussion is directed toward the flow meter 50, it should be noted that a variety of meters (e.g., pressure meters, temperature meters, flow meters, and the like) may be employed to detect sulfur deposition. For example, a pressure meter may detect a permanent pressure drop across the RO 46 as an indication of the sulfur deposition within each fluid conduit 32. Thus, the flow meter 50 is given by way of example, and is not intended to be limiting.

As illustrated, each fluid conduit 32 may also include an inlet temperature sensor 52, an inlet pressure sensor 54, and an outlet pressure sensor 56 relative to the RO 46. The sensors 52 and 54 are disposed upstream of the RO 46 and downstream of the inlet control valve 42. The outlet pressure sensor 56 is disposed downstream of the RO 46 and upstream of the outlet control valve 44. Each of the sensors 52, 54, 56 detects an operating condition associated with the fluid. In certain embodiments, a differential pressure instrument may include the pressure sensors 54 and 56. In other words, it may be desirable to sense a differential pressure across the RO 46. Thus, the sensors 54 and 56 may detect the upstream pressure, the downstream pressure, a differential pressure across the RO 46, or any combination thereof.

Operation of the sulfur detection system 16 may be adjusted based on the operating conditions. As noted earlier, it is desirable to selectively heat or cool the fluid conduits 32 to improve the operability of the sulfur detection system 16. Accordingly, a controller 54 is communicatively coupled to the temperature control jacket 36, the heating source 38, the cooling source 40, and/or the sensors 52, 54, and 56. The controller 54 includes one or more processors and/or memory components to adjust the operation of the sulfur detection system 16. For example, the controller 58 may estimate an outlet temperature of the fluid downstream of the RO 46. The outlet temperature may be estimated using the inlet temperature, the inlet pressure, and the outlet pressure using, for example, an equation of state. In addition, the controller 58 may adjust the temperature control jacket 36, the heating source 38, and/or the cooling source 40 based on the outlet temperature. For example, the outlet temperature may be too warm to encourage sulfur deposition within the fluid conduits 32 (i.e., the outlet temperature may be above a threshold temperature). The controller 58 may adjust the temperature control jacket 36, the heating source 38, and/or the cooling source 40 to decrease the outlet temperature to below the threshold temperature, thereby increasing the sulfur deposition rate and enabling faster detection of the sulfur concentration. After a sufficient amount of sulfur has deposited within the fluid conduits 32, the controller 58 may adjust the temperature control jacket 36 to increase the outlet temperature, thereby regenerating the fluid conduits 32. Additionally or alternatively, regeneration of the fluid conduits 32 may use a solvent wash 60 to dissolve the deposited sulfur. In such embodiments, the sulfur may then be extracted from the solvent to estimate the sulfur concentration.

In certain embodiments, the controller 58 may also estimate the sulfur concentration of the fluid based on the inlet and outlet conditions. For example, an inlet sulfur concentration may be defined by the inlet temperature and pressure, whereas an outlet sulfur concentration may be defined by the outlet temperature and pressure. The difference between the inlet and outlet sulfur concentrations may suggest a theoretical sulfur deposition rate on the RO 46. The theoretical sulfur deposition rate may be based on solubility curves, historical data, or a combination thereof. In addition, the theoretical sulfur deposition rate may be used to assess the validity of the flow rates detected by the flow meter 50.

The controller 58 is also communicatively coupled to the control valves 42 and 44, and the flow meter 50. Accordingly, the controller 58 may open or close the valves 42 and 44 to selectively enable or block flow to certain fluid conduits 32. As will be appreciated, it may be desirable to selectively isolate the fluid conduits 32 to enable sulfur deposition within certain fluid conduits 32, while blocking sulfur deposition within others. In addition, selectively isolating the fluid conduits 32 enables the flow meter 50 to detect flow rates through each individual fluid conduit 32 and allows for flow comparisons between the fluid conduits 32. Thus, the controller 58 may selectively open or close each of the control valves 42 and 44. As noted earlier, higher sulfur depositions are correlated with reduced flow rates through the fluid conduits 32. When the flow rate decreases below a minimum flow threshold, the controller 58 may open certain valves 42 or 44, and regenerate the fluid conduits 32 by adjusting the temperature control jacket 36. Operation of the sulfur detection system 16 is discussed further below in FIGS. 3-5.

FIG. 3 is a schematic diagram of a portion of the sulfur detection system 16. The sensors and the controller have been omitted for clarity. As illustrated, the fluid conduits 32 define a control line 62 and two exposed lines 64 and 66. As discussed previously, the control line 62 serves as a baseline of comparison to the two exposed lines 64 and 66. Thus, the control line 62 may be selectively isolated from the fluid for periods of time, in order to block sulfur deposition. In contrast, the exposed lines 64 and 66 may be exposed to the fluid for varying amounts of time to encourage sulfur deposition. In certain embodiments, the exposed lines 64 and 66 may be exposed to the fluid simultaneously or in an alternating manner. For example, the exposed line 64 may be a main operating line, while the exposed line 66 operates as a backup in case of maintenance on the exposed line 64. Additionally or alternatively, the exposed line 64 may operate while the exposed line 66 is being regenerated, and vice versa. Selection of the control lines and the exposed lines may be performed automatically by the controller 58, manually by an operator, or a combination thereof. In addition, the sulfur detection system 16 may include varying number of fluid conduits 32 (e.g., 2, 3, 4, 5, or more). Accordingly, the number of control lines and/or exposed lines may vary.

In the illustrated embodiment, an RO 68 of the exposed line 64 has a beta ratio $\beta_1$, and an RO 70 of the exposed line 66 has a beta ratio $\beta_2$. $\beta_2$ may be smaller than $\beta_1$, resulting in a faster detectable sulfur deposition rate within the exposed line 66. The difference in beta ratios is by way of example, and is not intended to be limiting. Indeed, each of the ROs 68 and 70 may have similar or identical beta ratios. As will be appreciated, the calculated sulfur concentration for each RO 68 and 70 may be approximately equal. In other words, the mass of the sulfur buildup on each RO 68 and 70 divided by the respective gas flows through each RO 68 and 70 may yield approximately equal sulfur concentrations. Accordingly, the ROs 68 and 70 may have a range of beta ratios to enable variable rates of sulfur deposition.

FIG. 4 is a graphical illustration 112 of a sulfur buildup in each fluid conduit 32 over time. In addition, FIG. 5 is a graphical illustration 114 of a mass flow rate of each fluid conduit 32 over time. Within FIG. 4, the control line 62 is represented by a solid line 116, the exposed line 64 is represented by a dashed line 118, and the exposed line 66 is represented by dotted line 120. Similarly, within FIG. 5, the control line 62 is represented by a solid line 122, the exposed line 64 is represented by the dashed line 124, and the exposed line 66 is represented by the dotted line 126. A baseline period is defined between $t_0$ and $t_1$. During the baseline period, each of the fluid conduits 32 is exposed to the fluid to establish a baseline flow. For example, the controller 58 may open valves 72 and 74 in the control line 62 and open the valves 76 and 78 in the exposed lines 64 and 66. The flow meter 50 may detect the flow rate through each of the fluid conduits 32. In certain embodiments, the baseline period may be relatively short, such that little to no sulfur deposition occurs, as is reflected in FIG. 4. As discussed earlier, increasing sulfur deposition may generally decrease the mass flow rate through the fluid conduits 32. Because there is little to no sulfur within the fluid conduits 32, the flow rate through each fluid conduit 32 may be at a local maximum during the baseline period, as shown in FIG. 5.

After the baseline period ends, an operation period is defined between $t_1$ and $t_2$. During the operation period, the controller 58 may selectively isolate the control line 62 while exposing the exposed lines 64 and 66. For example, the controller may close the control valves 72 and 74 in the control line 62 and open the control valves 76 and 78 in the exposed lines 64 and 66. At the start of the operation period $t_1$, sulfur begins to deposit on the ROs 68 and 70 of the respective exposed lines 64 and 66, thereby decreasing the flow rate in each exposed line 64 and 66. The sulfur deposition may be encouraged by adjusting the temperature of the exposed lines 64 and 66 using the temperature control jacket 36. As sulfur deposition continues, the geometry of the ROs 68 and 70 changes, resulting in accelerated sulfur deposition rates. As illustrated, the maximum sulfur deposition occurs toward the end of the operation period. In addition, because $\beta_2$ is smaller than $\beta_1$, sulfur deposition occurs more rapidly in the exposed line 66 than in the exposed line 64, which is reflected in FIG. 4. Consequently, the mass flow rate decreases more rapidly in the exposed line 66 than in the exposed line 64, as illustrated in FIG. 5.

A comparison period is defined between $t_2$ and $t_3$. The temperature of the fluid conduits 32 may be adjusted to reduce sulfur deposition during the comparison period. During the comparison period, each of the fluid conduits 32 is re-exposed to the fluid in order to determine the flow rates in each fluid conduit 32. The respective flow rates may be compared in order to estimate the sulfur concentration of the fluid. For example, the change in the flow rate of the exposed lines 64 and 66 may be used to quantify the buildup of sulfur on the respective ROs 68 and 70. In certain embodiments, the change in flow rates may be used to estimate an effective orifice diameter of the ROs 68 and 70. A sulfur concentration of the fluid may be estimated based on the flow rates, the effective orifice diameter, the operating temperature, the operating pressure, the pressure drop across the RO 46, the length of the operation period, the rate of deposition, or any combination thereof. In a presently contemplated embodiment, the sulfur concentration may be correlated based on empirical data (e.g., solubility curves for methane, ethane, or another hydrocarbon, or a mixture of hydrocarbons).

Operation of the sulfur detection system 16 during the comparison period is similar to operation during the baseline period. For example, the controller 58 may open valves 72 and 74 in the control line and open the valves 76 and 78 in the exposed lines. In certain embodiments, the comparison period may be relatively short, such that little to no sulfur deposition occurs, as is reflected in FIG. 4. In addition, the baseline and comparison periods may be shorter than the operation period. That is, the operation period may occur for hours or days, whereas the baseline and comparison periods may occur over a matter of minutes.

After the comparison period, the sulfur detection system 16 may return to the operation period. In other words, the flow rates detected during the comparison may serve as an additional or replacement baseline flow. Additionally or alternatively, the sulfur detection system 16 may enter a regeneration period, as defined between $t_3$ and $t_4$. During the regeneration period, each of the fluid conduits 32 is re-exposed to the fluid. As discussed earlier, the fluid conduits 32 may be regenerated with heat from the temperature control jacket 36 and/or with solvent from the solvent wash 60. The regeneration period may reduce the sulfur deposits in each fluid conduit 32 to approximately zero, such that the sulfur detection system 16 may return to operation in the baseline period. The operation of the sulfur detection system 16 is discussed further below with respect to FIG. 6.

Figure 6:
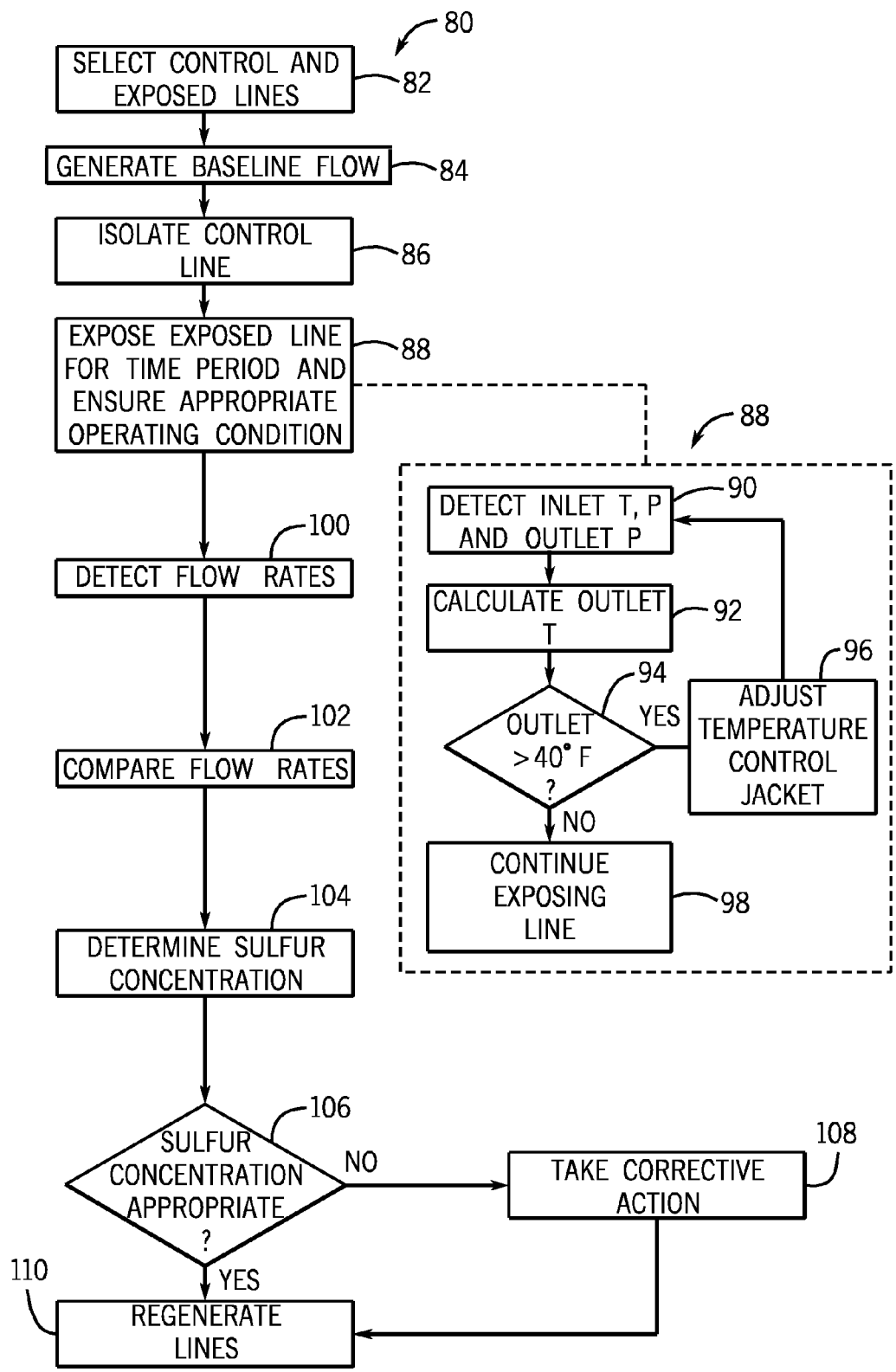
FIG. 6 is a flowchart of an embodiment of a method to detect sulfur in fluid streams.

FIG. 6 is a flowchart of an embodiment of a method 80 to detect the sulfur concentration of a fluid using the sulfur detection system 16. The steps described hereafter may be performed automatically by the controller 58 (e.g., performed by a controller as a result of one or more instructions stored on a tangible, non-transitory, machine-readable medium), manually by an operator, or both. Thus, although the method 80 is described within the context of the controller 58, portions of the method 80 may be implemented by the operator. The controller 58 may select (block 82) the control line 62 and the exposed line 64 among the plurality of fluid conduits 32. The controller 58 may generate (block 84) a baseline flow, which is detected by the flow meter 50, by exposing the control line 62 and the exposed line 64 to the fluid. After generating (block 84) the baseline flow, the controller 58 may selectively isolate (block 86) the control line 62 from the fluid. Isolation (block 86) of the control line 62 blocks sulfur deposition within the control line, enabling the control line 62 to serve as a basis of comparison at a later time. The controller may also selectively expose (block 88) the exposed line 64 to the fluid for a time period and ensure appropriate operating conditions.

In certain embodiments, ensuring appropriate operating conditions may include detecting (block 90) an inlet temperature, an inlet pressure, and an outlet pressure relative to the RO 46, using, for example, the sensors 52, 54, and 56. The controller 58 may then calculate (block 92) the outlet temperature using the detected operating conditions and an appropriate equation of state (e.g., ideal gas law or Peng-Robinson). The controller 58 may then determine (block 94) if the outlet temperature is above a temperature threshold. If the outlet temperature is above the temperature threshold, sulfur deposition may be slow. Thus, the controller 58 may adjust (block 96) the temperature control jacket 36 to decrease the temperature below the temperature threshold. However, if the outlet temperature is below the temperature threshold, the controller 58 may continue (block 98) to expose the exposed line 64. In certain embodiments, the temperature threshold may be based on a solubility of the sulfur at the inlet pressure, the outlet pressure, or both. The corresponding threshold temperatures may be between approximately 0° F. to 200° F. (−18° C. to 93° C.), 10° F. to 100° F. (−12° C. to 38° C.), or 20° F. to 60° F. (−6° C. to 16° C.), and all subranges in between.

Returning to the method 80, after the acts according to block 88, the controller 58 may then re-expose the fluid conduits 32 to the fluid, and the flow meter 50 may detect (block 100) the respective flow rates. The controller 58 may then compare (block 102) the flow rates. In certain embodiments, the controller 58 may compare (block 102) the flow rates between the control line 62 and the exposed line 64. Additionally or alternatively, the controller 58 may compare (block 102) the flow of the exposed line 64 over time. The controller 58 may then determine (block 104) the sulfur concentration based on various factors. The various factors may include the flow rate, the orifice diameter, the operating temperature, the operating pressure, the pressure drop across the RO 46, the length of the operation period, the rate of deposition, or any combination thereof. For example, the controller 58 may calculate an effective orifice diameter of the RO 46 of the exposed line 64 based on an initial orifice diameter, a final flow rate through the exposed line 64, and the baseline flow through the exposed line 64. The controller 58 may then correlate the effective orifice diameter of the RO 46 to a calibration curve relating the sulfur concentration to the effective orifice diameter and the time period of exposure. In a presently contemplated embodiment, the effective area of the RO 46 may be used to calculate a volume and/or mass of the sulfur deposit. That is, a displacement volume of the sulfur deposit may be calculated, from which a mass of the sulfur deposit may be estimated. The mass of the sulfur deposit may be divided by a volume of the fluid flow, thereby estimating a sulfur concentration of the fluid.

After determining (block 104) the estimated sulfur concentration, the controller 58 may determine (block 106) if the sulfur concentration is appropriate for the end user or the pipeline 20. If the sulfur concentration is not appropriate, the controller 58 may take (block 108) corrective action. Taking (block 108) corrective action may include increasing a temperature of the fluid within the pipeline 20, within the fuel source 12, within the gas turbine 14, or any combination thereof. Increasing the temperature of the fluid may generally increase the solubility of sulfur within the fluid, thereby decreasing the likelihood of sulfur deposition within the system 10. If the sulfur concentration is appropriate or after taking (block 108) corrective action, the controller 58 may regenerate (block 110) the control line 62 and the exposed line 64. Regeneration (block 110) may use the temperature control jacket 36, the solvent wash 60, or both, as discussed previously.

Technical effects of the invention include a sulfur detection system to quickly detect sulfur concentrations within a fluid. In particular, the sulfur detection system may detect a sulfur concentration of a gas stream by inducing sulfur deposition into an exposed line. The deposited sulfur from the gas stream may alter the geometry of the exposed line, resulting in a decreased the flow rate through the exposed line. In addition, a control line that is isolated from the gas stream may create a baseline of comparison to the exposed line. A sulfur concentration of the gas stream may then be determined by comparing the respective flow rates through the control line and the exposed line. As compared to large scale valves or infrastructure, the exposed line may have a smaller geometry, resulting in a relatively rapid sulfur deposition and detection. Operating conditions of upstream or downstream equipment may be adjusted in response to the detect sulfur concentration, thereby improving production rates and decreasing corrosion rates. For example, if the detected sulfur concentration is within a predetermined range, the temperature of upstream or downstream equipment may be increased to mitigate sulfur deposition.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A contaminant detection system, comprising:

a fluid path configured to flow a fluid comprising a contaminant concentration;

a meter disposed along the fluid path and configured to detect an operating parameter of the fluid flowing along the fluid path;

a plurality of fluid conduits disposed along the fluid path and forming a plurality of intermediate fluid paths configured to flow the fluid, wherein each fluid conduit of the plurality of fluid conduits comprises:

a restriction orifice (RO) having an orifice diameter configured to constrict one of the intermediate flow paths;

an inlet control valve disposed upstream of the RO; and an outlet control valve disposed downstream of the RO; and wherein the plurality of fluid conduits comprises a control line and a first exposed line; and a controller communicatively coupled to the meter and configured to isolate the control line from the fluid for a time period, to expose the first exposed line to the fluid for the time period, to expose the control line and the first exposed line to the fluid after the time period elapses, and to estimate the contaminant concentration using at least a change in the operating parameter over the time period.

2. The system of claim 1, wherein the contaminant comprises sulfur.

3. The system of claim 1, wherein the operating condition comprises a flow rate and the meter comprises a flow meter, or the operating condition comprises a pressure and the meter comprises a pressure transducer, or a combination thereof.

4. The system of claim 1, wherein the plurality of fluid conduits comprises a second exposed line, and the controller is configured to expose the second exposed line to the fluid for the time period and after the time period elapses.

5. The system of claim 4, wherein the controller is configured to expose the first and the second exposed lines to the fluid simultaneously.

6. The system of claim 1, wherein the plurality of fluid conduits comprises a second exposed line, and the controller is configured to expose the second exposed line to the fluid for the time period and after the time period elapses, the second exposed line comprises a second inner diameter and a second RO having a second orifice diameter, and the first ratio is greater than the second ratio.

7. The system of claim 1, comprising:

a filter disposed along the fluid path;

an inlet capillary manifold disposed downstream of the filter and configured to direct the fluid into the intermediate fluid paths;

a temperature control jacket disposed along the fluid path and downstream of the inlet capillary manifold and configured to selectively heat or cool the plurality of fluid conduits; and an outlet capillary manifold disposed along the fluid path and downstream of the intermediate fluid paths, and the outlet capillary manifold is configured to combine respective flows from the intermediate fluid paths into a combined flow along the fluid path.

8. The system of claim 7, wherein each fluid conduit of the plurality of fluid conduits comprises:

an inlet temperature sensor disposed upstream of the RO and configured to sense an upstream temperature of the fluid;

an inlet pressure sensor disposed upstream of the RO and configured to sense an upstream pressure of the fluid; and an outlet pressure sensor disposed downstream of the RO and configured to sense a downstream pressure of the fluid, wherein the controller is communicatively coupled to the respective inlet temperature sensors, the inlet pressure sensors, and the outlet pressure sensors of the plurality of fluid conduits, and the controller is configured to calculate a downstream temperature of the fluid within each intermediate fluid path using at least the upstream temperature, the upstream pressure, and the downstream pressure sensed for the respective intermediate fluid path, and wherein the controller is configured to adjust the temperature control jacket to maintain the downstream temperature below a temperature threshold.

9. A method, comprising:
selecting a control line and an exposed line from a plurality of fluid conduits using a controller;
detecting a baseline operating parameter for the control line and the exposed line using a meter;
isolating the control line for a time period using one or more control valves;
exposing the exposed line for the time period using the one or more control valves;
exposing the exposed line and the control line after the time period elapses;
detecting a first operating parameter through the control line and a second operating parameter through the exposed line using the meter; and
determining a concentration of a contaminant of a fluid based at least in part on the first operating parameter, the second operating parameter, the baseline operating parameter, and the time period.

10. The method of claim 9, comprising maintaining appropriate operating conditions, comprising:
detecting an inlet temperature, an inlet pressure, and an outlet pressure of the fluid relative to a restriction orifice within the exposed line using one or more sensors;
calculating an outlet temperature based at least in part on the inlet temperature, the inlet pressure, and the outlet pressure of the fluid using the controller;
determining if the outlet temperature is above a temperature threshold using the controller; and
decreasing the inlet temperature when the outlet temperature is above the temperature threshold using a temperature control jacket.

11. The method of claim 10, wherein the contaminant comprises sulfur or a sulfur-containing compound, and wherein the temperature threshold is based on a solubility of the sulfur or the sulfur-containing compound within the fluid at the inlet pressure, or the outlet pressure, or both.

12. The method of claim 9, wherein detecting the first and second operating parameters comprises:
exposing the control line and isolating the exposed line using the one or more control valves;
detecting the first operating parameter of the control line using the meter;
isolating the control line and exposing the exposed line using the one or more control valves; and
detecting the second operating parameter of the exposed line using the meter.

13. The method of claim 9, comprising regenerating the exposed line by increasing an inlet temperature of the fluid within the exposed line using a temperature control jacket.

14. The method of claim 9, comprising taking corrective action when the concentration of the contaminant is above a threshold concentration, and wherein taking corrective action comprises increasing an upstream temperature of the fluid within a main pipeline, a gas wellhead, a gas processing plant, or a gas turbine engine.

15. The method of claim 9, wherein determining the concentration of the contaminant comprises:
calculating an effective orifice diameter of a restriction orifice (RO) of the exposed line based at least in part on an initial orifice diameter of the RO, the second operating parameter, and the baseline flow; and
correlating the effective orifice diameter to the concentration of the contaminant based at least in part on the effective orifice diameter and the time period.

16. A sulfur detection system, comprising:
a fluid path configured to flow a fluid comprising a sulfur concentration;
a flow meter disposed along the fluid path and configured to detect a flow rate of the fluid;
a control line defining a first intermediate fluid path, wherein the control line comprises a first restriction orifice (RO) comprising a first orifice diameter configured to constrict the first intermediate fluid path, a first inlet control valve disposed upstream of the first RO, and a first outlet control valve disposed downstream of the first RO, wherein the first orifice diameter is less than a first diameter of the first intermediate fluid path;
an exposed line defining a second intermediate fluid path, wherein the exposed line comprises a second restriction orifice comprising a second orifice diameter configured to constrict the second intermediate fluid path and configured to capture sulfur from the fluid, a second inlet control valve disposed upstream of the second RO, and a second outlet control valve disposed downstream of the second RO, wherein the second orifice diameter is less than a second diameter of the second intermediate fluid path; and
a controller communicatively coupled to the first and second inlet control valves and the first and second outlet control valves, wherein the controller is configured to selectively isolate or expose the control line and the exposed line by adjusting the first and second inlet control valves and the first and second outlet control valves; and
wherein the controller is configured to isolate the control line from the fluid for a time period, expose the exposed line to the fluid for the time period, expose the control line and the exposed line to the fluid after the time period elapses, and to determine a sulfur concentration of the fluid based at least in part on a change in the flow rate over the time period.

17. The system of claim 16, comprising a temperature control jacket configured to heat or cool the control line, the exposed line, or both, wherein the controller is configured to automatically increase a temperature of the exposed line to reduce the sulfur captured on the second restriction orifice when the flow rate is below a flow threshold.

18. The system of claim 16, wherein the controller is configured to:
calculate a downstream temperature relative to the second RO based on an upstream temperature, an upstream pressure, and a downstream pressure relative to the second RO; and
calculate a sulfur deposition based on the upstream and downstream temperatures and the upstream and downstream pressures.

19. The system of claim 1, wherein the RO comprises a plate disposed within the fluid conduit, and the plate comprises a hole having the orifice diameter.

20. The system of claim 19, wherein the RO is configured to encourage deposition of the contaminant on the plate to cause constriction of the orifice diameter.

* * * * *